US006462004B2

(12) United States Patent
Farrell et al.

(10) Patent No.: US 6,462,004 B2

(45) Date of Patent: *Oct. 8, 2002

(54) SYNTHETIC BAR COMPOSITIONS PROVIDING SOURCE OF DIVALENT CATIONS AVAILABLE AT CRITICAL POINT TO ENHANCE BAR PROCESSING

(75) Inventors: Terence James Farrell, Tenafly, NJ (US); John Richard Nicholson, Ramsey, NJ (US); Keith Francis, Clifton, NJ (US)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/779,073

(22) Filed: Feb. 8, 2001

(65) Prior Publication Data

US 2002/0039977 A1 Apr. 4, 2002

Related U.S. Application Data

(63) Continuation-in-part of application No. 09/632,064, filed on Aug. 3, 2000, now abandoned.

(51) Int. Cl.[7] .................................................. A61K 7/50

(52) U.S. Cl. ....................... 510/152; 510/153; 510/155; 510/156; 510/508

(58) Field of Search ................................. 510/152, 153, 510/155, 156, 508

(56) References Cited

U.S. PATENT DOCUMENTS

| | | | |
|---|---|---|---|
| 4,557,853 A | 12/1985 | Collins | |
| 5,869,441 A | 2/1999 | Fair et al. | |
| 5,981,451 A | 11/1999 | Farrell et al. | |
| 6,121,216 A | 9/2000 | Narath et al. | 510/152 |

FOREIGN PATENT DOCUMENTS

| | | |
|---|---|---|
| WO | 95/13356 | 5/1996 |

*Primary Examiner*—Necholus Ogden

(74) *Attorney, Agent, or Firm*—Ronald A. Koatz

(57) ABSTRACT

The invention provides bar compositions comprising anionic surfactant, soap, free fatty acid and source of divalent cation sufficiently soluble to precipitate soluble soaps found in the molten process used to make the bars. By this interaction, improved finishing properties are observed.

8 Claims, 1 Drawing Sheet

SYNTHETIC BAR COMPOSITIONS PROVIDING SOURCE OF DIVALENT CATIONS AVAILABLE AT CRITICAL POINT TO ENHANCE BAR PROCESSING

The subject application is a continuation-in-part application of U.S. Ser. No. 09/632,064, now abandoned, which was filed Aug. 3, 2000.

FIELD OF THE INVENTION

The present invention relates to bar compositions comprising synthetic anionic surfactant, fatty acid soap and free fatty acid and to improved processes of making such bars, particularly with higher quantities of essentially water soluble soap (e.g., soap having solubility equal to or greater than 82/18 tallow coconut soap) than previously thought possible. The invention refers particularly to compositions made using a molten mix process, i.e., where ingredients are mixed at temperatures above about 110° F. before the molten composition is chilled, optionally refined and/or milled, plodded to extrudate (generally in form of extruded "logs") and cut and stamped into final bars. It is in these molten mix processes where higher levels of soluble soaps are associated with materials becoming soft and sticky and causing finishing problems, especially those related to bar stamping.

BACKGROUND OF THE INVENTION

It is well known to make extruded bar compositions using synthetic anionics (e.g., acyl isethionates, alkyl glyceryl ether sulfates etc.) and fatty acid soap.

The soap in such compositions is generally known to serve a number of purposes. First, it serves to help structure the bars so that they do not readily crumble both when the bar is being "finished" (e.g., extruded, stamped) and also as a final user bar. Fatty acid soap also provides some beneficial user properties such as good lather and a certain skin feel which may be desirable to some consumers. In addition, soap is generally cheaper than most anionics and provides some cost savings.

Despite the advantages noted above, however, the level of soap which can be used in the process for making these bars (e.g., molten process in which ingredients are mixed at a temperatures above about 110° F.) and in which soap is not the main surfactant, has generally been considered to have a cap because excessive levels lead to poor bar finishing properties (e.g. principally in that the bars are stickier and result in problems in bar extrusion and stamping when these stickier bars stick to the machinery). Thus, in a bar typically containing 30–75% of a non-soap anionic surfactant, preferably 35–60% anionic, levels of soluble soap above 5% can lead to the above noted finishing problems.

Without wishing to be bound by theory, at least part of this problem is believed to be due to the fact that increasing soap levels generates soap solutions and/or lyotropic liquid crystal phases with unbound water within the synthetic detergent (syndet) bar formulation. The presence of such phases have the potential to hinder the finishing stages of production, which includes extrusion and stamping, by rendering the material soft and sticky.

Unexpectedly, applicants have found that if a source of divalent cation is provided such that the divalent cation is made available to the mix solution (e.g., to be made available, the source component must have solubility equal to or greater than that of calcium carbonate); and sufficient divalent ion is made available to react with the soluble soap dissolved in the unbound water, the degree of softness and stickiness during final bar production can be lessened or alleviated. Moreover, the use of cation does not significantly affect the foam values of the bars and, even at high levels of cation, acceptable foam values are achieved (e.g., 150 ml or greater as measured in defined foam value test).

U.S. Pat. No. 5,981,451 to Farrell et al. relates to a process for making bars containing a mixture of anionic surfactant and soap but there the process is a non-molten process and the stickiness issues of finishing a bar are primarily encountered when using a molten mix process.

U.S. Pat. No. 4,557,853 to Collins relates to bars containing alkaline earth metal carbonates as skin feel agents. Given the low water solubility of these carbonates, it is believed that the level used (2.4%–5.9% earth metal carbonate as defined by the surfactant to earth metal carbonate ratio) is too low to provide a sufficient amount of divalent ion to control the level of soluble soap in solution. That is, the patent fails to recognize the link between providing available divalent cation which can insolubilize the soap at a certain point in the process and thereby reduce stickiness during the finishing stages of bar processing. It should also be noted that the finishing process is considerably less likely to suffer from soft, sticky material issues when soap is the predominant constituent of the formulation.

WO 95/13356 to Procter & Gamble relates to an acyl isethionate bar containing liquid polyols and magnesium soap. The bars of the subject invention do not require liquid polyols of this reference. (However unnecessary the use of liquid polyols in the subject invention, it should be noted that the inventors do not wish to exclude the possibility of using liquid polyols in formulations). Moreover, the patent does not recognize the need for providing available/excess divalent cations (e.g. to aid as scavengers for otherwise soluble soap during molten mixing where, if not removed, they are believed to be the cause of down-stream "finishing" problems). On the contrary, the patent requires the magnesium soap to stay bound and act as a filler/process aid.

U.S. Pat. No. 5,869,441 to Fair et al. discloses bar compositions comprising novel chelating surfactants derived from ethylenediaminetriacetic acid (EDTA). However, this reference differs from bars of the subject invention for a number of reasons.

First, the subject invention is an extrusion process. The Fair patent is not limited to any process but is probably best suited for cast melt or injection molding process. This is because, for example, levels of most amphoterics (claim (1)(c)) above 3% in synthetic formulation would be almost impossible to extrude and maintain acceptable lather. Similarly with claim (1)(e), if levels of PEG, free fatty acid etc. are used at above 40%, it would be extremely difficult to extrude. In short, Fair simply does not teach or recognize that, in an extrusion process, high levels of multivalent help extrusion when soluble soaps are included in the formula.

Further, one major reason Fair et al. avoids multivalent ions (i.e., they must be used at levels below 1% by wt.) is because they significantly depress lather. That is EDTA is by nature a sequestering agent. In the presence of high levels of soluble, multivalent, inorganic salts, EDTA loses surfactancy, via chelation, resulting in poor lather. As noted, Fair et al. fails to recognize the importance of the presence of multivalent ions in the presence of soluble soaps. Bars of the subject invention may have less than 1% multivalent ions and may also have more than 1% multivalent. Indeed, much higher levels are tolerable while maintaining adequate foaming (e.g., >150 ml).

BRIEF DESCRIPTION OF THE INVENTION

More particularly, the subject invention comprises:

(1) 20% to 75%, preferably 35% to 60% by wt. of an anionic surfactant, preferably alkali metal salt of alkyl isethionate;

(2) about 4 to 20%, more preferably greater than 6 to 12% of a fatty acid soap or soap fraction having a solubility equal to or greater than 82/18 tallow/coconut soap i.e., solubility of 1.1 g/l in water at 40° C.);

(3) 4% to 30%, preferably 10 to 25% free fatty acid;

(4) compound or compounds which is a source of divalent cation; which compound is used in an amount sufficient that, when the divalent source compound is solubilized, it provides sufficient available cation to interact with soluble soap fraction (e.g., tallow/coconut soap mixture) such that there is less soluble soap and an enhancement in bar throughput; said enhancement in throughput being defined either by greater extrusion rate and/or greater number of bars stamped per minute.

The solubility of the divalent cation source may affect the amount of the compound used in the process. Thus, it should be understood, for example, that more calcium carbonate may be needed because the solubility of calcium carbonate is low while, for a more soluble salt such as magnesium or calcium chloride, much lower amounts may be required.

Finally, the use of cation does not affect foam values of the bar even at high levels. Acceptable foam values (>150 ml) are found, for example, even at equivalent of 5% calcium chloride in the formulation.

Figure 1:
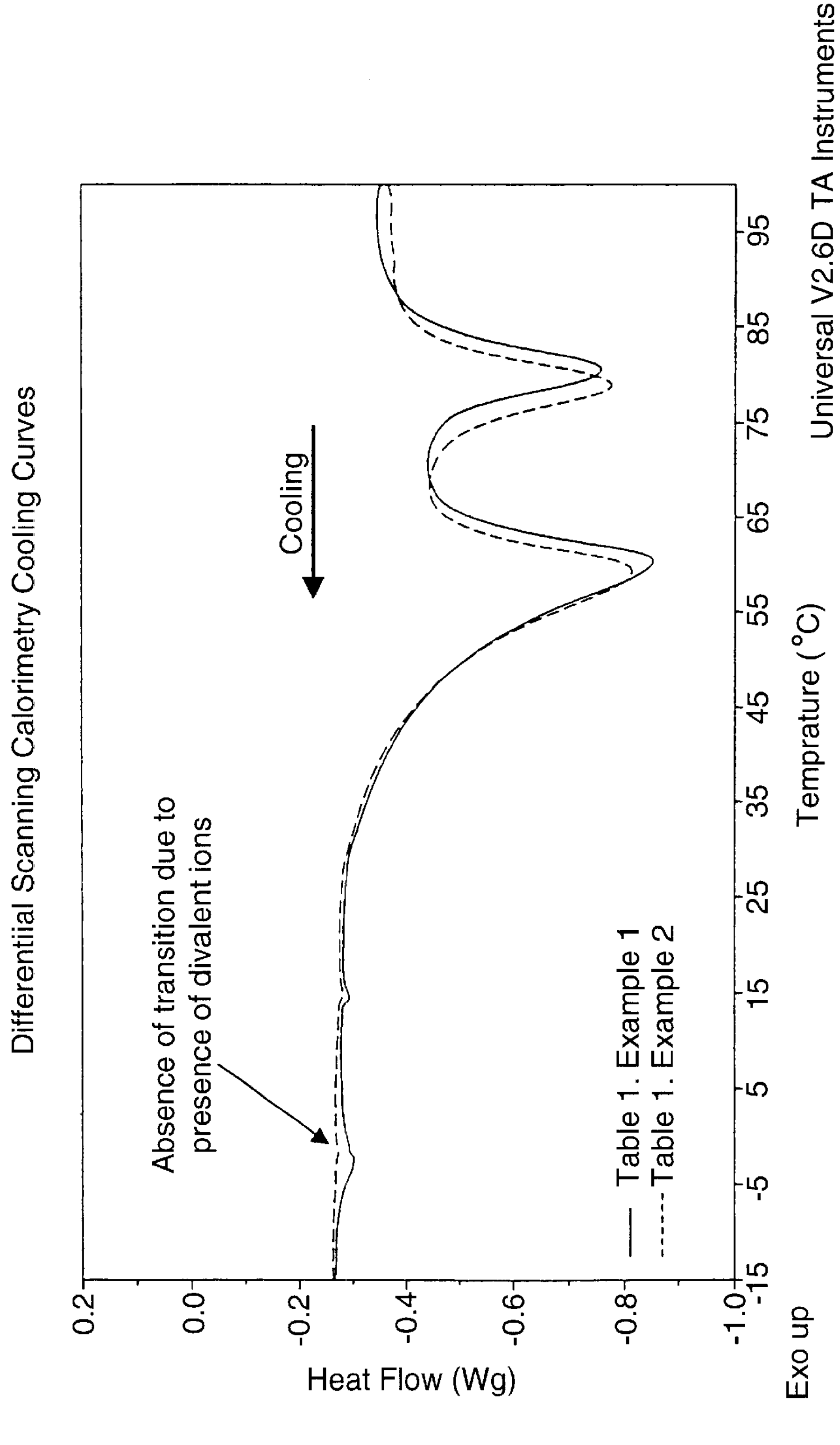
FIG. 1 is a graph of differential scanning calorimetry cooling curves. The critical point of this graph is the peak represented at about 0° C. in the cooling cycle for Formulations 1 (solid line formulation without calcium carbonate) and 2 (dashed formulation with calcium carbonate).

Specifically, when calcium carbonate was added (dashed line), there is no transition, presumably because ions bind to soluble soap. Since there is less soluble soap, this leads to enhanced properties downstream.

DETAILED DESCRIPTION OF THE INVENTION

The present invention is directed to bars comprising synthetic anionic surfactant: in combination with greater amounts of fatty acid soap (e.g., soluble fatty acid soap) than previously believed possible without affecting stickiness of bars and bar finishing properties (e.g., extrudability, stampability). More specifically, the invention is directed to the unexpected discovery that addition of sufficient amount of a compound(s) providing available divalent cation to insolubilize the greater amounts of soluble soap found when such greater amounts of soap are used in a molten mix process will in turn permit the use of bars having these high soap levels while avoiding problems associated with the higher soap levels. Higher soap content is generally more economical in that it allows soap to replace generally more expensive synthetic surfactant.

In particular, the invention is concerned with bars made by an extrusion process in which components are mixed at molten temperature (>110° F.), cooled (for example, on chip cooler), optionally refined and/or milled, cut and stamped. By providing these divalent cations, it is believed the cations can precipitate soluble soaps (thereby reducing the total amount of soluble soap as a percent of the total soap such that there is less soluble soap thereby resulting in higher stampability). This in turn is believed to eliminate/decrease phases created by the soluble soaps which otherwise would lead to the formation of a sticky composition. Because of reduced stickiness, the bar will extrude and stamp better (improved "finishing" properties) and have superior final bar user properties.

Each of the components of the bars are set forth in greater detail below.

Anionic

A first required component of the bar compositions of the invention is that they must have at least one anionic surfactant.

The anionic surfactant which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

$$R^1O_2CCH_2CH(SO_3M)CO_2M;$$

and amide-MEA sulfosuccinates of the formula:

$$R^1CONHCH_2CH_2O_2CCH_2CH(SO_3M)CO_2M$$

wherein $R^1$ ranges from $C_8$–$C_{22}$ alkyl and M is a solubilizing cation.

Taurates are generally identified by the formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

A preferred anionic is acyl isethionate, e.g., $C_8$ to $C_{18}$ acyl isethionate. These esters are generally prepared by reaction between alkali metal isethionate with mixed aliphatic fatty acids having from 6 to 18 carbon atoms and an iodine value of less than 20. Generally at least 75% of the mixed fatty acids have 12 to 18 carbons and up to 25% have from 6 to 10 carbons. The isethionate may also be an alkoxylated isethionate as described in U.S. Pat. No. 5,393,466 to Ilardi et al. hereby incorporated by reference into the subject application.

Of course, mixtures of one or more anionics may be used.

Generally, the anionic(s) will comprise 20–75%, preferably 35–60% by wt. of bar composition.

Fatty Acid Soap

A second required component of the invention is the use of certain soluble "soap". As previously noted, the use of levels of soluble soap above 4% by wt., particularly levels beyond 10% has been previously discouraged, particularly in systems comprising, for example, acyl isethionate, free fatty acid and alkali metal isethionate (see for example, U.S. Pat. No. 4,954,282 to Rys et al. and particularly, column 4, lines 10–13). This is not only because soap is generally harsher than other anionics, but also because syndets, such as those based on acyl isethionates, can become soft and sticky in the presence, for example, of >4% by wt. soluble soap thereby causing process problems at later steps when bars are extruded and stamped (e.g., sticking to dies).

In the subject invention, soaps may comprise 4–20%, preferably 6–12% by wt. of the final bar.

By soluble soap is meant a soap or soap fraction having a solubility equal to or greater than 82/18 tallow/coconut soap. The solubility of 82/18 tallow/coconut may be defined in turn as solubility of 1.1 g/l in water at 40° C.

82/18 soap generally refers to mixture of about 15% to about 20% coconut oil and about 80% to about 85% tallow. These mixtures contain about 95% fatty acids having about 12 to about 18 carbon atoms. The soap may be prepared from coconut oils in which case the fatty acid content is about 85% of $C_{12}$–$C_{18}$ chain length.

In a preferred embodiment of the invention, fatty acid soap comprises 4 to 20% by wt., preferably 6 to 12% by wt. of the bar.

In addition to specific "soluble" soap, additional soaps, which may not be as soluble, may be used.

The term "soap" is used here in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural of synthetic aliphatic (alkanoic or alkenoic) acids having about 12 to 22 carbon atoms, preferably about 12 to about 18 carbon atoms. They may be described as alkali metal carboxylates of acrylic hydrocarbons having about 12 to about 22 carbon atoms.

The soaps may contain unsaturation in accordance with commercially acceptable standards. Excessive saturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Free Fatty Acid

Another required component of the invention are $C_8$ to $C_{22}$ carbon free fatty acids. These may function in part as superfatting agents and/or as skin feel and creaminess enhancers. Superfatting agents may be $C_{10}$–$C_{18,}$ preferably $C_{10}$–$C_{16}$ fatty acids. A preferred skin feel and creaminess enhancer is stearic acid. These fatty acids may comprise 4 to 30%, preferably 10 to 25% by wt. of the bar composition.

Divalent Cation Source Compounds

Another required component of the subject invention is a compound or compounds which is a source of divalent cation. While the compound may be any compound which is a salt having such a divalent counterion (e.g., calcium $2^+$ or magnesium $2^+$), the solubility of the salt is also critical since enough of the divalent cation must be made available (i.e., the compound must be sufficiently soluble) and it must be available in sufficient quantity so that there is enhanced throughput at the stamping stage.

Thus, for example, if the compound is calcium carbonate, since this is far less soluble than calcium chloride, it may require 10 or 12% calcium carbonate or more to provide sufficient available cation to ensure the soluble soap component is precipitated. On the other hand, far less calcium or magnesium chloride would be required to ensure the same result.

The critical point, as noted, is that sufficient cation is made available to ensure most of the soluble soap is bound to the cations so it becomes essentially insoluble.

Looking at FIG. 1, it can be seen that what this does is to eliminate/decrease the phase transition at about 0° C. so that it becomes essentially flat (left side of FIG. 1, where the absence of transition is shown by the dashed line).

Although this may not appear significant, what this accomplishes is to substantially reduce the stickiness of the bar downstream so that, when the compositions are cooled, extruded, cut and stamped, at the extrusion and stamping phase far less residue gets stuck to the machinery. This in turn leads to enhanced extrusion rate (as measured, for example, by pounds extruded per minute and/or bars stamped per minute).

Examples of compounds which may be used include slightly less soluble salts such as calcium or magnesium carbonate or more soluble salts such as calcium or magnesium chloride. Preferably, the compound should have solubility at least that of calcium carbonate (at 18° C., solubility of 0.0013 g/100 grams water as defined in Kirk-Othmer Chemical Engineering Encyclopedia). Other divalent cations which may be used with the compounds include group IIA metals (besides calcium and magnesium) such as berrylium, strontium and barium.

As noted, the amount of compounds used will vary with the solubility of the compound, but, ultimately must be used in an amount sufficient so that enhanced stamping (relative to total starting soap) is obtained after the cations have had a chance to bind. This in turn may be measured by an improvement in the extrusion (measured for example in pounds extruded per minute or number of bars stamped per minute). Ideally, increase in extrusion or bar rate should be 10% or greater (e.g., 10–200%, preferably 10 to 100%), preferably 15% to 150%, more preferably 20% to 125%. It should be understood that percent improvement is intended to be based on otherwise exact or similar process conditioning (e.g., screw speeds, barrel temperatures and other parameters that would be understood by those skilled in the art being same or substantially the same) such that the improvement is based on addition of cations alone.

Optionals

In addition to ingredients noted above the bar compositions may have other surfactants selected from the group consisting of nonionic, amphoteric, cationic etc.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

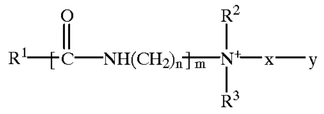

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

x is alkylene of 1 to 3 carbon atoms optionally substituted with hydroxyl, and y is $—CO_2—$ or $—SO_3—$ Suitable amphoteric detergents within the above general formula include simple betaines of formula:

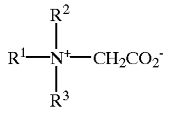

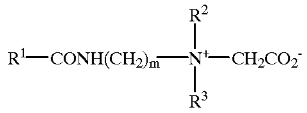

where m is 2 or 3.

In both formulae $R^1$ is alkyl or alkenyl of 7 to 18 carbons; and $R^2$ and $R^3$ are independently alkyl, hydroxyalkyl or carboxy alkyl of 1 to 3 carbons. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

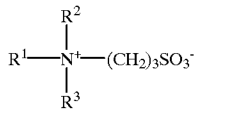

or

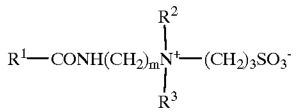

where m is 2 or 3, or variants of these in which $—(CH_2)_3SO_3—$ is replaced by

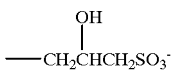

In these formulae $R^1$, $R^2$ and $R^3$ are as discussed for the amido betaine.

Amphoteric surfactant generally comprises 1% to 10% of the bar composition.

Other surfactants (i.e., nonionics, cationics) may also be optionally used although these generally would not comprise more than 0.01 to 10% b wt. of the bar composition.

Nonionic surfactants include in particular the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference and polyhydroxyamides such as described in U.S. Pat. No. 5,312,954 to Letton et al., hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Volume I & II) by Schwartz, Perry & Berch, both of which are also incorporated into the subject application by reference.

Skin mildness improvers also preferably used in the composition of the invention are salts of isethionate. Effective salts cations may be selected from the group consisting of alkali metal, alkaline earth metal, ammonium, alkyl ammonium and mono-, di- or tri-alkanol ammonium ions. Specifically preferred cations include sodium, potassium, lithium, calcium, magnesium, ammonium, triethyl ammonium, monoethanolammonium, diethanolammonium or triethanolammonium ions.

Particularly preferred as a mildness improver is simple, unsubstituted sodium isethionate.

The skin mildness improver will be present from about 0.5% to about 50%. Preferably, the mildness improver is present from about 1% to about 25%, more preferably from about 2% to about 15%, optimally from 3% to 10% by weight of the total composition.

Other performance chemicals and adjuncts may be needed with these compositions. The amount of these chemicals and adjuncts may range from about 1% to about 40% by weight of the total composition. For instance, from 2 to 10% of a suds-boosting detergent salt may be incorporated. Illustrative of this type additive are salts selected from the group consisting of alkali metal and organic amine higher aliphatic fatty alcohol sulfates, alkyl aryl sulfonates, and the higher aliphatic fatty acid taurinates.

Adjunct materials including germicides, perfumes, colorants, pigments such as titanium dioxide and water may also be present.

Of course, the bars may also comprise oil soluble benefit agents (e.g., silicone, petrolatum etc.) or water soluble benefit agents (e.g., alpha hydroxy acids) as are well known to those skilled in the art (see for example broad list of benefit agent discussed at column 8, lines 14–67 of U.S. Pat. No. 6,066,613 to Tsaur et al., hereby incorporated by reference into the subject application).

Processing

Through several processes all the ingredients, less the perfume, are combined in a mixer suitable for mixing viscous materials. The process is run at a temperature which insures homogeneity of the batch, typically between 180°–240° Fahrenheit. When the target moisture has been achieved, the product is removed from the mixer and cooled forming either chips or noodles. The cooled material is then combined with perfume and tumbled to ensure an even distribution of perfume throughout the product. The perfumed material is then transported to a hopper which feeds a refiner, which in turn feeds a plodder. The billet which exits the plodder is then cut, stamped into a bar and packaged.

The only criticality within the process is that the divalent ion be present during the molten mixing stage in order to react with the soluble soap.

The bars of the invention maintain good foam values even at relatively high level of cation (e.g., 5% calcium chloride).

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Applicants prepared the following 4 formulations as described in the Process Section above.

TABLE 1

| | Formulation | | | |
|---|---|---|---|---|
| | #1 (Comparative) | #2 | #3 | #4 |
| Sodium Cocoyl Isethionate | 40.00 | 40.00 | 40.00 | 40.00 |
| Stearic/Palmitic Acid | 23.00 | 23.00 | 23.00 | 23.00 |
| Sodium Isethionate | 3.00 | 3.00 | 3.00 | 3.00 |
| Zwitterionic Surfactant | 1.50 | 1.50 | 1.50 | 1.50 |
| Na Stearate | 4.00 | 4.00 | 4.00 | 4.00 |
| 82/18 Tallow/Coconut Soap | 8.00 | 8.00 | 8.00 | 8.00 |
| Talc | 8.00 | 0.00 | 8.00 | 8.00 |
| Ca Carbonate | 0.00 | 8.00 | 0.00 | 0.00 |
| TiO2 | 0.35 | 0.35 | 0.35 | 0.35 |
| Calcium Chloride | 0.00 | 0.00 | 0.80 | 0.00 |
| Magnesium Chloride | 0.00 | 0.00 | 0.00 | 0.80 |
| Sodium Chloride | 0.80 | 0.80 | 0.00 | 0.00 |
| Coconut fatty acid | 3.50 | 3.50 | 3.50 | 3.50 |
| Water | 6.00 | 6.00 | 6.00 | 6.00 |
| Misc. | qs. to 100% | qs. to 100% | qs. to 100% | qs. to 100% |

In order to show advantages of the invention, applicants first compared Formulation 1, Table 1 (Comparative) to Formulation 2, Table 1. Each formulation was extruded and the rate of extrusion was measured by weighing the billets exiting the plodder over a given period of time. Several measurements were taken and the averages were as follows:

Formulation with talc, rate of extrusion: 4.7 lb. per minute

Formulation with calcium carbonate, rate of extrusion: 5.7 lb. per minute

As noted from above, by incorporating calcium carbonate into the formulation the rate of extrusion increased by 20%.

Applicants also compared Formulation 1, Table 1 (Comparative) to Formulation 2, Table 1 under separate circumstances than Example 1. The formulations were compared based on the maximum, sustainable rate of bars which could be stamped per minute, under a given set of conditions, on a Binacchi commercial stamper. Formulation 1 could be sustained at 350 bpm (bars per minute). Formulation 2 could be sustained at 420 bpm. By incorporating calcium carbonate into the formulation the stamping rate has increased by over 20%.

The examples clearly show the advantage of using divalent compounds during molten mixing.

Examples 5–8

In order to show advantages of bar of the invention over, for example, U.S. Pat. No. 5,869,441 to Fair, applicants prepared various formulations as noted below.

TABLE 2

| | Formulation | | |
|---|---|---|---|
| | #5 (Comparative) | #6 | #7 |
| Sodium Cocoyl Isethionate | 40.00 | 40.00 | 40.00 |
| Stearic/Palmitic Acid | 23.00 | 23.00 | 23.00 |
| Sodium Isethionate | 3.00 | 3.00 | 3.00 |
| Zwitterionic Surfactant | 1.50 | 1.50 | 1.50 |
| C12—C18 Sodium Soaps | 12.00 | 12.00 | 12.00 |
| Calcium Carbonate | 8.0 | — | — |
| Titanium Dioxide | 0.35 | 0.35 | 0.35 |
| Talc | — | 8.0 | 8.0 |
| Coconut Fatty Acid | 3.5 | 3.5 | 3.5 |
| Sodium Chloride | 1.2 | — | — |
| Calcium Chloride | — | 1.2 | — |
| Magnesium Chloride | — | — | 1.2 |
| Water | 6.00 | 6.00 | 6.00 |
| Misc. | Qs. to 100% | Qs. to 100% | Qs. to 100% |
| Foam Volume* | 210 ml | 195 ml | 230 ml |

*As a control a 2% solution of a commercial DOVE bar was prepared and the foam volume was 230 ml.

The calculated foam values noted above were obtained as follows:

40–50 ml of surfactant solution was placed into a graduated cylinder (typically 250 ml), and the cylinder was capped and shaken thoroughly for a fixed amount of time (30 sec). Specifically, 2% solutions of the extruded bars were made, and 50 ml of the solutions was placed into a 250 ml graduated cylinder with a glass stopper. The stopper was shaken vigorously for 30 seconds and the foam volume was finally read.

A fourth solution (Example 8) was also prepared and tested for foam volume. To 50 ml of a 2% solution of comparative #7 above, 0.05 gm of calcium chloride was dissolved. This level represents the amount of calcium chloride which would be in solution if the formulation included 5.0% wt. calcium chloride. The foam volume was measured as 160 ml. There is a decrease in lather volume, but this example does demonstrate that relatively high loadings (much higher than that stated in Fair et al.) of divalent ions in this formulation space still produce acceptable foam volumes.

By contrast, and as seen from Table 2 of U.S. Pat. No. 5,869,441 to Fair (Column 13, Example 4) reproduced below, lather volume was completely dampened with presence of aluminum or magnesium chloride:

TABLE

| Lather Volume of the Surfactant Solutions With and Without Multi-Valence Ions | |
|---|---|
| Compositions | Lather Volume (ml) |
| 2.5% wt. Na-LED 3A* | 124 |
| 2.5% wt. Na-LED 3A<br>2.5% wt. Aluminum Chloride | 39 |
| 2.5% wt. Na-LED 3A<br>2.5% wt. Magnesium Chloride | 2 |

*Ethylenediaminetriacetic acid-derived anionic surfactant

The example thus clearly shows that bars of the subject invention are further characterized by minimum foaming levels as defined.

What is claimed is:

1. Bar composition comprising:

(1) 20% to 75% by wt. of an anionic surfactant;

(2) 4% to 20% fatty acid soap or soap fraction having solubility equal to or greater than 82/18 tallow/coconut soap;

(3) 4% to 30% free fatty acid;

(4) compound or compounds which is source of divalent cation when solubilized at a temperature of about 0° C. which compound is used in an amount sufficient that, when the divalent source compound is solubilized at a temperature of about 0° C., it provides sufficient available cation to interact with soluble soap or fraction such that the level of soluble soap is reduced and an enhancement in bar throughput is achieved, wherein said enhancement is defined by greater extrusion and/or greater number of bars stamped per minute;

wherein bar composition maintains lather volume of 150 ml or greater when measured by cylinder shaking method even at levels greater than 1% divalent cation.

2. A composition according to claim 1, comprising 35–60% anionic surfactant.

3. A composition according to claim 1, wherein anionic surfactant is acyl isethionate.

4. A composition according to claim 1, comprising 6 to 12% fatty acid soap.

5. A composition according to claim 1, wherein solubility of tallow/coconut is 1.1 g/l in water at 40° C.

6. A composition according to claim 1, wherein divalent cation is a group IIA metal selected from the group consisting of magnesium, calcium, berrylium, strontium, barium and mixtures thereof.

7. A composition according to claim 1, wherein improvement in extrusion is 10% or greater, wherein all other variables are substantially the same.

8. A composition according to claim 1, wherein improvement in bars stamped per minute is 10% or greater, wherein all the other variables are substantially the same.

* * * * *